United States Patent [19]

Perlman

[11] Patent Number: 5,302,344
[45] Date of Patent: Apr. 12, 1994

[54] METHOD FOR CONTAINMENT OF A LABORATORY CHEMICAL

[75] Inventor: Daniel Perlman, Arlington, Mass.

[73] Assignee: Brandeis University, Waltham, Mass.

[21] Appl. No.: 606,466

[22] Filed: Oct. 31, 1990

[51] Int. Cl.⁵ .............................................. A61L 2/06
[52] U.S. Cl. ................................ 422/26; 229/3.5 MF; 53/425; 428/35.8; 428/216; 428/458; 428/334
[58] Field of Search .................. 428/35.8, 216, 334, 428/458; 53/425; 422/26; 229/3.5 MF

[56] References Cited

U.S. PATENT DOCUMENTS

| | | | |
|---|---|---|---|
| Re. 31,137 | 2/1983 | Ossian et al. | 156/244.11 |
| 3,892,058 | 7/1975 | Komatsu et al. | 53/21 |
| 3,935,810 | 2/1976 | Milano | 229/3.5 MF X |
| 3,949,114 | 4/1976 | Viola et al. | 428/337 |
| 3,984,604 | 10/1976 | King et al. | 428/411.1 |
| 4,058,632 | 11/1977 | Evans et al. | 426/126 |
| 4,172,914 | 10/1979 | Festag et al. | 428/35.9 |
| 4,291,085 | 9/1981 | Ito et al. | 428/215 |
| 4,308,084 | 12/1981 | Ohtisuki et al. | 156/233 |
| 4,310,578 | 1/1982 | Katsura et al. | 428/35.3 |
| 4,311,742 | 1/1982 | Otsuka | 428/35.4 |
| 4,360,551 | 11/1982 | Guarino et al. | 428/35.3 |
| 4,370,388 | 1/1983 | Mito et al. | 428/461 |
| 4,389,438 | 6/1983 | Ohtsuki et al. | 428/35.9 |
| 4,407,689 | 10/1983 | Ohtsuki et al. | 156/243 |
| 4,528,234 | 7/1985 | Kaiho et al. | 428/216 |
| 4,533,576 | 8/1985 | Tanahashi et al. | 428/35 |
| 4,559,266 | 12/1985 | Misasa et al. | 428/341 |
| 4,737,548 | 4/1988 | Kojima et al. | 525/193 |
| 4,756,917 | 7/1988 | Kamada et al. | 428/457 |
| 4,767,673 | 8/1988 | Nakano et al. | 428/458 |
| 4,769,261 | 9/1988 | Hazelton et al. | 428/35.4 |
| 4,774,134 | 9/1988 | Kehe et al. | 428/335 |
| 4,868,033 | 9/1989 | Nakano et al. | 428/201 |
| 4,957,820 | 9/1990 | Heyes et al. | 428/458 |
| 4,965,135 | 10/1990 | Im et al. | 428/475.8 X |
| 5,145,737 | 9/1992 | Boiron et al. | 428/458 |

Primary Examiner—James C. Housel
Assistant Examiner—Jeffrey R. Snay
Attorney, Agent, or Firm—Lyon & Lyon

[57] ABSTRACT

A method for containment of a laboratory chemical or device during a procedure chosen from weighing, physical transfer, storage, incubation and sterilization. The method includes provision of a repeatedly foldable layered sheet which includes both an aluminum foil layer and a plastic layer, and selection of the plastic layer to be unreactive with caustic chemicals and organic solvents. The layered sheet can be folded and unfolded along a crease at least five times and steam autoclaved without structural failure. The sheet is oriented with its plastic layer toward the laboratory chemical or device and is folded and shaped to form a protector which covers the chemical or device.

16 Claims, No Drawings

METHOD FOR CONTAINMENT OF A LABORATORY CHEMICAL

BACKGROUND OF THE INVENTION

This invention relates to methods for containing chemicals and objects.

Guarino et al., U.S. Pat. No. 4,360,551 describes a flexible plastic film laminate adapted for use in the manufacture of a retortable pouch for food packaging. The laminate includes a layer of heat-sealable polyolefin, a binary layer of metallized thermoplastic polymer, and an adhesive to bond the layers. Katsura et al., U.S. Pat. No. 4,310,578, Evans et al., U.S. Pat. No. 4,058,632, Tanahashi et al., U.S. Pat. No. 4,533,576, Viola et al., U.S. Pat. No. 3,949,114, and Ossian et al., U.S. Pat. No. 4,190,477, and U.S. Pat. No. Re. 31,137 describe other flexible film laminate materials and methods for manufacturing materials including combinations of a polyolefin layer and other resin coatings bonded to both surfaces of an aluminum foil layer.

A single heat-shrinkable plastic layer bonded to one surface of a metal foil layer via an intermediate resin or adhesive layer is described for use in electromagnetic shielding and packaging by Nakano et al., U.S. Pat. No. 4,767,673. The heat-shrinkable layer of Nakano et al., which may be a polyolefin layer, causes the foil to wrinkle and contract in overall dimension.

Various foldable and non-foldable (i.e., elastic) sheet materials have been used in the laboratory to form closures and containers. Native aluminum foil is used as a foldable wrapping material for laboratory items which are to be autoclaved; a stretchable self-adherent plastic laboratory film (Parafilm ®; manufactured by American Can Corp.) is used to form a water-tight closure on a test tube or other container; a polyvinylidine wrap (Saran Wrap ™) is used for wrapping various devices; and a high density polyethylene (HDPE) sheet is used as an autoclave containment bag for sterilizing biological waste.

SUMMARY OF THE INVENTION

This invention relates to the use of a repeatedly foldable (refoldable) foil-backed polyolefin sheet. A polyolefin film is bonded or laminated to a sufficient thickness of aluminum foil to provide a layered sheet material which may be bent to hold a shape and which may be repeatedly folded and reused without cracking or tearing. The sheet may be used in research and clinical laboratories to form a variety of shaped containers and shaped covers for test tubes, flasks and the like which may be heated and subjected to caustic chemicals. It also relates to the use of a "dead-folding" (i.e. folding with little to no elastic spring-back) laminated plastic wrap which is chemically inert and withstands steam autoclaving so that, as a wrapping material, it may be used to maintain sterility and chemical purity of autoclaved objects, chemicals and aqueous chemical solutions. The sheet is also resistant to many organic solvents and is therefore useful as a foldable covering material for beakers, test tubes and other containers holding such chemical solutions. The foil layer in the laminate structure additionally provides a barrier to light.

Aluminum foil as a foldable wrapping material is susceptible to attack by corrosive acids, bases and salts so that its utility in the chemical laboratory is limited. Furthermore, the excessive and sharp creasing of aluminum foil coupled with its physical weakness, including its susceptibility to tearing, puncture and creasing places further limits on its utility. For example, a double thickness of aluminum foil is typically used in sterile wrapping procedures to guard against contamination through pin holes or other accidental penetrations of the foil. Aluminum foil is seldom used for holding liquids or solid chemicals, or for wrapping heavy or sharp objects due to its physical and chemical susceptibilities.

The present invention provides a layered sheet including a chemically inert polyolefin layer reinforced by an aluminum foil backing layer for use in a laboratory. The foldable layered polyolefin-foil sheet is used for construction of chemically resistant laboratory devices which previously could not be fabricated from either the above described plastic wrap or native aluminum foil. The layered sheet is resistant to tearing and puncture and thus permits a single thickness of material to be utilized for making refoldable coverings, envelopes, and the like, which are used in wrapping objects for steam autoclave sterilization. The plastic layer simultaneously serves to strengthen and chemically protect the aluminum foil while preventing excessively sharp creasing of the foil which leads to metal fatigue. The plastic layer is also exploited for its ability to decrease problematic sliding friction between aluminum foil and objects wrapped in foil. Undesirable trace metal contamination of laboratory materials contained or wrapped in aluminum foil is also eliminated by the presence of the interposed plastic layer.

Many plastic materials have been used to form laboratory containers and other equipment, such as test tubes, beakers, flasks, funnels, and trays, for storing, transferring, incubating, or autoclaving laboratory chemicals. These include polyethylene, polypropylene, polystyrene, polyacrylate, polyvinyl, polycarbonate, and polytetrafluoroethylene. As discussed above, flexible wrapping sheet materials including aluminum foil, and plastics such as polyvinylidine cling wrap, (eg. Saran Wrap ™) and Parafilm ® laboratory plastic stretch wrap (American National Can Corp.) are commonly used for covering laboratory vessels. Although these flexible wrapping materials are waterproof, they have the disadvantage of poor durability and are generally not used to form containers for storing or transferring chemical solids or liquids. In addition, while some of these materials are chemically resistant, they either lack thermal stability (i.e., are not resistant to steam autoclaving) and fail to hold a shape (in the case of plastic wraps), or if they hold a shape, fail to posses requisite chemical stability in the presence of salts and other chemicals. Parafilm ® plastic wrap, for example, lacks stability in the presence of organic solvents and melts at about 65°–70° C., far below autoclave temperatures of approximately 121° C.

Thus, in a first aspect, the invention features a method for protecting any one of a variety of laboratory chemicals and devices during several common laboratory procedures including weighing, physical transfer, storage, incubation and sterilization (e.g., using gamma irradiation or steam autoclaving), by providing a refoldable layered wrapping sheet constructed from an aluminum foil layer approximately 0.0005–0.002 inches thick and a plastic layer less than or approximately equal to this foil thickness disposed on and bonded to one side of the foil layer. The plastic layer is unreactive with common caustic chemicals and organic solvents. Furthermore, the composite layered wrapping sheet can be folded and unfolded at least five times along a fixed line, and also steam-autoclaved at 120° C., without structural failure. In practice, a sized portion of the layered sheet is selected, the plastic-coated side of the sheet is oriented toward the chemical or device being protected, and the sheet is folded and shaped one or more times to form a protector which covers or contains the chemical or device before carrying out one of the described procedures.

In a related aspect, the invention features a laboratory chemical or device protected during a procedure including weighing, transfer, storage, incubation and sterilization by a dead-folding layered sheet having the above-stated characteristics.

In preferred embodiments, the method provides protection of laboratory chemicals and devices by use of a foldable layered sheet which can withstand repeated folding (at least 5 cycles of folding and unfolding along a fixed line) without cracking or tearing. The sheet can also withstand washing and drying without cracking or tearing, allowing multiple cycles of reuse.

In other preferred embodiments, the plastic layer is a polyolefin or polyester plastic, e.g., polypropylene, high density polyethylene or polyethylene terephthalate; the plastic layer is biaxially oriented, and bonded to the aluminum foil layer with either a bonding adhesive or an extruded laminating resin, e.g., polyurethane bonding adhesive or high density polyethylene extruded laminating resin. An additional protective plastic coating can be optionally applied to the foil layer on the side opposite the original plastic layer; and shaped and sized portions of the layered sheet are cut, stacked and packaged for convenience of use.

The invention features the use of a layered sheet including a chemically unreactive plastic layer or film of a limited thickness which is supported by and bonded to aluminum foil of a sufficient thickness for the folding characteristic of the foil to dominate and be controlling over the elastic and poor folding of the plastic layer. Such a sheet allows the construction of various protection and containment means for laboratory chemicals and devices. The foldable, low friction plastic surfaced sheet functions to maintain chemical and sterile isolation of the material being protected or contained during laboratory procedures including weighing, physical transfer, storage, incubation and sterilization (e.g., using gamma irradiation or steam autoclaving). The plastic layer of the layered sheet is selected to provide the chemical isolation (and add strength and puncture resistance to the foil) while being limited in thickness to allow the foil to continue providing the important dead-folding characteristic to the layered sheet. The plastic layer also functions to provide a bending radius to folds in the layered sheet thereby reducing metal fatigue associated with sharp creasing of aluminum foil. This bending feature permits repeated folding along a line in the layered sheet without resultant structural failure, i.e., cracking, puncturing or tearing. Reduced metal fatigue also allows recycling the layered sheet for reuse which typically requires washing, drying, smoothing and sometimes re-rolling the sheet for storage prior to reuse. That is, such recycling, including washing, results in multiple cycles of bending and unbending of the sheet. Without the reduction in metal fatigue provided by the plastic layer, the foil would experience structural failure, e.g., tearing (commonly experienced in attempting to wash and reuse aluminum foil). The lubricity of the plastic layer which contacts wrapped objects also functions to reduce the substantial sliding friction which normally affects aluminum foil-wrapped objects, such as glass pipets, especially after they have been steam autoclave-sterilized. Thus, a pipet can be easily removed from a plastic-layered protective wrapping of the present invention by sliding the pipet out along its longitudinal axis. The plastic layer also prevents trace metal (aluminum) contamination of the pipet.

Unlike many plastic-foil laminate sheets used in the food packaging industry to form retort pouches (which usually comprise a thermoplastic sandwich employing a thin foil layer as a gas diffusion barrier in the middle), the present invention features the use of a relatively thick aluminum foil layer (about 1 mil) for retaining folded shapes, and a layer of plastic, preferably polyolefin plastic, a substantial coating (about 0.5–1.5 mils) of which is applied to only one side of the foil. Applicant has found that the use of this foil-dominated structure is important for maintaining the essentially inelastic folding property, (also known as "dead-folding") of the aluminum foil. If a substantial plastic coating or layer (defined as a plastic coating greater than approximately 0.50 mil in thickness) is applied to both sides of an aluminum foil of comparable thickness, the dead-folding property of the foil is compromised and, when bent, the sandwiched foil tends to unbend owing to the elastic memory of the structure. Furthermore, applicant has found that while the thickness of the protective reinforcing plastic layer, which is preferably a polyolefin plastic layer, may be as great as the foil layer, it should not be substantially greater than the thickness of the foil if the foil's dead-folding property is to be preserved.

Other features and advantages of the invention will be apparent from the following description of the preferred embodiments thereof, and from the claims.

DESCRIPTION OF THE PREFERRED EMBODIMENTS

Foldable Plastic and Foil Layered Sheet

The following are examples of laminates of the present invention. Those skilled in the art will recognize that these examples are not limiting to this invention and that equivalent laminates can be readily formed without undue experimentation. A layered plastic and foil structure includes a layer of aluminum foil 0.50–2.0 mil thick, preferably 0.75–1.25 mil thick, (e.g., Alcoa 1145-0 foil, Davenport, Iowa) onto which is bonded a layer of chemically inert, flexible plastic which has a melting point above 121° C. and is essentially unreactive with caustic chemicals such as strong acids, e.g., HCl and $H_2SO_4$, alkalis, e.g., NaOH and $NH_4OH$ and common organic solvents, e.g., alcohol, acetone, ether, carbon tetrachloride and other hydrocarbon solvents. This layer may, for example, consist of polypropylene (PP), high density polyethylene (HDPE), polyethylene terephthalate (PET), polysulfone or polyetherimide. Preferably the plastic is a low-stretch polyolefin plastic, such as biaxially oriented polypropylene (PP) or, high density polyethylene (HDPE), but a polyester plastic such as polyethylene terephthalate (PET) may alternatively be utilized. Neither PP nor PET is presently commercially available as a direct extrusion product on aluminum foil. Rather, the preferred biaxially oriented (low-stretch) cast PP (manufactured by the Bemis Company) and PET films (manufactured by the E.I. DuPont Company) may be bonded to the foil using either a glue-like adhesive bonding agent or a hot extruded laminating resin such as high density polyethylene.

Adhesive agents such as polyurethane adhesive are selected which sustain the integrity of HDPE, PET, and PP-foil laminate structures at autoclave temperatures of at least 121° C. For example, PET and HDPE layers ranging from 0.4 mil to 1.5 mil thickness were adhesively bonded to aluminum foil (Alcoa Corp., 1145-0 foil) using a polyurethane adhesive (Alcoa Corp., F-358 urethane adhesive for HDPE and F-354 for PET). Other appropriate adhesives having suitable stability under steam autoclave conditions include epoxy resin, ethylene vinyl acetate copolymer, and maleic anhydride adducts of ethylene-propylene copolymer.

Results from tests in which these laminates were subjected to successive cycles of autoclaving (20 min, 121° C.) followed by 10 minute surface exposure (on plastic face only) to acetone and carbon tetrachloride followed by concentrated HCl, showed that PP, PET and HDPE coatings were compatible with steam sterilization and caustic and organic chemical exposure.

Further experiments were carried out to compare the relative resistance to tearing of two laminates, one including 1.0 mil HDPE and the other, 0.5 mil PET each separately bonded to 1.0 mil aluminum foil. The 0.5 mil PET film, (which as a cast biaxially oriented free sheet material is considerably more resistant to stretch than 1.0 mil HDPE) was found to provide the aluminum foil laminates with substantially greater resistance to tearing. For the purpose of laboratory device fabrication in the present invention, resistance to structural failure is important (i.e., the laminate does not tear or crack following repeated folding and unfolding of the sheet along a single line following at least five cycles of creasing one way and then the other). Temperature stability and chemical resistance are also important. An aluminum foil laminated structure including 0.5 mil thick PET, (approximately 0.25-1.0 mil thick PET), was adhesively bonded to 1.0 mil aluminum foil (approximately 0.25-1.5 mil thick foil) using polyurethane adhesive which was applied in an amount of approximately 0.67 pounds per 1000 ft.$^2$ (Alcoa Corporation). The resulting laminated foil proved to be a strong, puncture-resistant and tear-resistant material suitable for use in the present invention.

A somewhat different laminated structure in which the polyurethane adhesive was replaced by a hot extruded laminating resin consisting of approximately 0.5-0.75 mil HDPE resin to yield a 2.0-2.25 mil thick PET-HDPE-aluminum foil laminated structure (0.5 mil PET, 0.5-0.75 mil HDPE, 1.0 mil aluminum foil laminate, manufactured for applicant by the Ludlow Corp., Homer LA) was also investigated and found useful for the purpose of this invention. Heat set, balanced, biaxially oriented PP films ranging in thickness between 0.5-1.0 mil and which were similarly bonded to 1.0 mil aluminum foil using the same HDPE resin were also useful in this invention.

Flexible foil laminate laboratory devices which are conveniently fabricated using the above-described material are described below. The utility of this material in laboratory devices may be understood by comparing the performance of such devices with that of devices fabricated from conventional foil. As a group, the laminated material devices possess the "dead-fold" property of aluminum foil, i.e., the ability to be easily and firmly folded. This dead-fold property is critical, for example, in molding and wrapping the foil laminate material over containers and flask openings to prevent escape of volatile or caustic chemicals and vapors. Applicant has found that if the thickness of a polyolefin coating does not substantially exceed the thickness of the accompanying foil, the "dead-fold" quality of the laminated foil will still compare favorably with native aluminum foil for the purposes of this invention. Applicant has also found that the undesirable susceptibility of household and industrial aluminum wrapping foil to physical and chemical damage in the course of its laboratory use is largely eliminated by addition of the polyolefin layer. Thus, a laminated plastic foil comprising 1.0 mil aluminum foil laminated with either 0.5-1.0, mil biaxially oriented PEP, PP or 1.0 mil HDPE can, be tightly folded, formed or bent into a variety of shapes but at the same time, is surprisingly resistant to inadvertent kinking and creasing. It is this property that is critical in this invention. A comparative examination of creases produced in foils by manually folding 1.0 mil aluminum foil either with or without a 0.5 mil PET laminated coating, showed that the PET coating provided an additional radius of curvature within the crease while the native aluminum foil showed a very sharp crease with little bending radius. More specifically, the PET-coated foil when folded back on itself using approximately 2 lb. per in$^2$ of pressure (with the plastic surface inward) formed a soft fold with an intersheet airspace of approximately 0.020 inches while the uncoated aluminum foil formed a hard crease with only a 0.002 inch air space. Laminates described above and having this soft fold property are useful in this invention. Applicant believes that the larger bending radius evident in the coated foil reduces metal fatigue during bending and folding, and allows as many approximately 100 cycles of folding and unfolding the sheet along a given fold without cracking or tearing of the foil. Such is not the case with uncoated foil. In forming laboratory devices from laminated foil, the polyolefin layer also beneficially reduces the tendency of foil to accumulate spontaneous and undesirable surface kinks and creases. Thereby the tendency of dry chemical powder residues and chemical solution residues to remain in these creases is diminished. The radius of curvature in the laminated material also allows repeated folding and unfolding with reduced metal fatigue thereby increasing the durability of the material. Additional beneficial properties associated with the increased physical strength and chemical resistance imparted to the laminated foil by the polyolefin layer are discussed below in the context of individual flexible laboratory devices.

It is noted that an additional but thin (less than or approximately equal to 0.5 mil) protective plastic coating constituting a chemical barrier coating may optionally be added to the side of the foil opposite the original polyolefin layer to impart chemical resistance. This additional protective coating preferably consists of an autoclave-resistant and chemically inert polyolefin resin such as HDPE. The coating must not substantially compromise the dead-fold property of the laminated foil to be useful in the present invention. It is also noted that for convenience in using the presently described sheet material it may be cut, slit or die-cut into predetermined shaped and sized portions and then stacked and packaged for convenience of use. For example, packaged stacks of die-cut squares and circles are particularly useful for allowing rapid covering of large numbers of chemical sample tubes, flasks, beakers, and the like.

Plastic-layered foil sheets suitable for use in this invention are described above. The examples which follow, illustrate a variety of applications for these laminated sheets involving protection of laboratory chemicals and devices.

EXAMPLE 1

Chemical Weighing Dish

Dry chemical reagents to be weighted are commonly dispensed into shallow disposable polyethylene or aluminum dishes which are placed, in turn, on the pan of a weighing balance. Caustic chemicals (which may also be hygroscopic) such as sodium hydroxide pellets cannot be placed in aluminum weighing dishes because they are susceptible to corrosion. Polyethylene weighing dishes, on the other hand tolerate caustic chemicals but offer little protection from ambient humidity and little protection against spillage.

The laminates comprising 1 mil aluminum foil and 0.5–1.0 mil PET, HDPE or PP have been used to form disposable weighing dishes (formed by bending squares of the laminate sheet over a clean square block of plastic to form a walled square dish). Once a caustic chemical has been placed in the dish for weighing (polyolefin surface facing the chemical), the dish may be folded inward and closed over the chemical to protect the chemical from ambient moisture, light, and/or spillage prior to further transfer, transport, or use of the chemical.

EXAMPLE 2

Chemical Funnel

Glass and plastic (usually polyethylene or polypropylene) funnels are commonly used in transferring dry chemicals, solvents, and solutions into flasks and other containers. Often, an appropriately sized funnel with a sufficiently large exit tube cannot be located. The laminates described in Example 1 have been used to form chemical funnels as needed, by folding circles of the laminate sheet into cones (plastic surface inward) and cutting off the tip of the cones to allow passage of material. The cone is held in appropriate position with a ring support or alternatively with one hand while the chemical to be transferred is poured using the other hand. Native aluminum foil which is susceptible to salts and caustic chemicals cannot be generally used in this application.

EXAMPLE 3

Chemical Containment Tray

Concentrated acid and alkaline solutions as well as a variety of organic solvents which are typically toxic are often stored in laboratories in a containment basin positioned within a chemical fume hood. For purposes of safety and cleanliness it is desirable to segregate acids, alkalis and organic solvents (to prevent accidental cross-reaction) in such storage areas. The polyolefin aluminum foil laminates described in Example 1 have been used to form raised edge-containment and storage trays for chemical reagents located in such basins and fume hoods. The plastic surface which is used face-up, is non-reactive with the above groups of chemicals and prevents any pin-hole formation in the foil which would allow escape of the caustic solutions and subsequent corrosion of the aluminum.

EXAMPLE 4

Sterile Pipet Sheaths and Canister

Conventional aluminum foil has often been used to wrap individual pipets and groups of pipets prior to their autoclaving. The foil provides a sterile storage wrapping or sheath which is removed at the time of pipet use. It is common practice to wrap at least two thicknesses of foil around pipets to assure sterility in the event that occasional pin-holes traverse one layer of the foil. To remove to the pipet at the time of use, it is usually necessary to unwrap the pipet, due to friction (preventing sliding) between the pipet and the autoclaved (and slightly oxidized) aluminum foil. In contrast, the polyolefin surface of the aluminum foil laminates of Example 1 is not susceptible to oxidation and provides an excellent autoclave wrap for protecting and storing sterile pipets. The laminate materials are resistant to pin-hole formation thereby allowing a minimum of material to be used in the wrapping process. Furthermore, when the plastic surface is oriented inward and contacts the pipet(s), the sliding friction between the pipet(s) and the sheath is minimized. This allows the sterile pipet to be rapidly removed from the sheath by sliding it along its longitudinal axis without having to unwrap or tear the sheath covering the barrel of the pipet. Furthermore, the absence of contact between the aluminum surface and the glass pipet eliminates trace metal contamination of the pipet. When using native aluminum foil to wrap pipets, applicant has determined that the autoclave sterilization process causes traces of aluminum oxide to be deposited on the pipet and, depending upon the end-use of the pipet, such trace-metal contamination may or may not be problematic. For example, in pipetting operations involving aluminum assay or involving biochemical and chemical system inhibited by traces of aluminum, this contamination is harmful.

EXAMPLE 5

Chemical Reaction Vessel and Liner

In carrying out a chemical reaction involving one or more caustic reagents, oxidizing or reducing agents, or organic solvents, a chemically inert reaction vessel must be utilized. Glass, ceramic, plastic, and metal materials have been previously used for such vessels. The aluminum foil-plastic laminate materials in Example 1 have now been used to make disposable reaction vessels. This laminate material has been shaped for such vessels by forming it (with the plastic surface inward) over clean laboratory beakers, for example, so as to assume the shape of the beaker. The resulting vessel may be used unsupported, or alternatively placed inside a larger beaker thereby serving as a disposable liner. For example, when mixing polymerizing adhesive materials (e.g. epoxy resins) it is convenient to use the laminate material as a vessel liner during chemical mixing. Following mixing, the viscous resin may be conveniently dispensed from the foil vessel by pouring or squeezing out the resin contents. Alternatively the foil vessel may be stretched flat again to allow trowel and other spreading tool access to the resin. Of significance for many chemical reactions, the foil layer of the laminate allows rapid thermal equilibration of chemical components placed in such vessels while the polyolefin layer provides the physical reinforcement, puncture-resistance, and chemical stability of the vessel.

EXAMPLE 6

Chemical and Radiochemical Isolation Sheet

When working with hazardous liquids including caustic acids, alkalis, toxic and carcinogenic agents, and other biohazardous materials, and radioactive isotope solutions, it is important to protect the work area and to prevent contamination of surrounding surface areas. Two materials currently utilized for protecting working surfaces against such contamination are plastic-backed absorbent paper sheet and aluminum foil. A number of laboratory operations have been identified in which a polyolefin-aluminum foil laminated sheet material (see Example 1) provides a protective barrier and working surface which is superior to the other available materials. These laboratory operations generally involve maintaining a chemically inert and chemically clean working surface on which pipets, spatulas and other chemically dedicated transfer devices can be rested and, if necessary, from which surface droplets or small spills of valuable liquid samples may be easily recovered. A paper absorbent sheet does not allow such recovery and, simple native aluminum foil does not provide the chemically inert barrier required for resting pipets which have been used in caustic solutions. The plastic laminated foil allows these procedures to be successfully completed, in addition to providing a material more resistant to accidental puncture. In the case of radioisotope solution manipulations, the resistance of the foil laminate material to puncture and potential leakage of radioactive liquids is particularly significant.

EXAMPLE 7

Refoldable Autoclave Envelope

A variety of devices utilized in bacteriological and clinical-diagnostic laboratories are packaged as multiple units in a flexible wrapping material and subjected to steam autoclaving. The resulting sterile packages may be opened and closed many times to remove sterile units one at a time. Multiple sterile filters or stacked cotton velvets for bacterial replica-plating have been wrapped in brown craft paper or aluminum foil. The disadvantages with using each of these wrapping materials include the presence of steam-extractable binder materials (in craft paper) which may contaminate clean objects, and the susceptibility to tearing and pin-hole formation (in aluminum foil) during repeated unfolding and refolding. The use of a polyolefin-laminated aluminum foil to form a refoldable autoclave envelope solves both of the above problems. Such an envelope may simply be formed by taking a square sheet of material and folding two parallel sides over one another and then folding over the two ends. The laminates described in Example 1 contain essentially no steam-extractable contaminants and also withstand repeated folding and unfolding operations without structural degradation. (See discussion above, regarding the foil bending radius contributed by the plastic coating).

EXAMPLE 8

Septum for Sample Tube Storage

Two aluminum foil laminate sheet materials described in Example 1 have been successfully used as septum sheets for retaining and storing small (0.5–1.5 ml capacity) sample tubes such as microcentrifuge tubes. In this use, the flexible material substitutes for a rigid storage rack as follows: A sample tube storage rack is selected for a group of tubes (the tubes preferably have a flange-lipped style so that they may be lip-supported). An overhanging sheet of laminated foil is placed on top of the rack and the flanged tubes (preferably having a conical tip) are pushed down through the foil until their flanged lip rests on the foil. The extra overhanging flap of laminated foil may be folded over the top of the tubes to cover the tubes and secure them downward against the underlying foil septum (which now supports the tubes). The foil sheet and captured tubes may now be lifted from the rack and stored elsewhere thereby freeing the rack for other use. Alternatively the septum sheet may be left on the rack and used to secure the tubes in the rack itself (friction between the tubes and septum prevents the tubes from falling out of the rack).

It has been found that native aluminum foil cannot readily be used for the above-described purpose because it is susceptible to further tearing around the punctures in the foil created by the inserted tubes (the tubes may then fall through and be lost). The polyolefin-reinforced foil however, is resistant to further tearing and provides a chemically resistant polymer surface which may be folded over and used to cover the chemical samples.

EXAMPLE 9

Refoldable Light-Excluding Envelope for Autoradiography

Exposure of an electrophoretic slab gel containing radioactively tagged materials to X-ray film is a process by which the location of radioactive materials in that gel can be established. Such a process known as gel autoradiography must be carried out in the dark and often employs a medical X-ray film cassette for this purpose. However, in the laboratory it is also common to utilize plain aluminum foil to exclude light and to immobilize the gel against the film. However, aluminum foil is susceptible to pin-hole light leaks and tears during folding and unfolding. Consequently it is common to utilize two or three layers of foil to prevent light leaks. It has been found that a superior envelope can be formed for gel autoradiography using the foil laminates described in Example 1. A single thickness of laminated foil provides a secure and essentially "pin-hole proof" envelope enclosure which furthermore may be repeatedly folded and unfolded without structural failure to provide access to the film and gel. Thus an improved economy of use of aluminum foil is achieved with the present laminate material as well as an improved reliability vis a vis accidental light leaks.

EXAMPLE 10

Flexible Cap for Containers Holding Chemical Solutions

Test tubes, flasks, beakers and graduated cylinders are often used as receptacles for caustic solutions and organic solvents. As such, neither aluminum foil nor Parafilm ® laboratory film can be universally utilized to cover the above containers holding these liquids; caustic solutions attack aluminum and organic solvents attack Parafilm ®. Foil-backed HDPE or PP films as described in Example 1 can however be utilized to safely cover all of these liquids contained within these receptacles. Furthermore, as folded-over tightly fitting flexible caps which are stable to temperatures of at least 120° C., these containers and their solutions may be heated or even autoclaved for sterilization.

Other features and embodiments are within the following claims.

I claim:

1. A method for containment of a laboratory chemical or device during a procedure selected from the group consisting of weighing, physical transfer, storage, incubation and sterilization comprising the steps of:

providing a repeatedly foldable layered sheet comprising an aluminum foil layer having a first thickness of between 0.0005 inches and 0.002 inches and a plastic layer having a second thickness less than or substantially equal to said first thickness disposed on one side of and bonded to said foil layer, said plastic layer being unreactive with caustic chemicals and organic solvents, wherein said layered sheet can be folded and unfolded along a line at least five times without structural failure and wherein said layered sheet can be steam autoclaved at approximately 120° C. without structural failure and wherein said sheet possesses the dead-fold property of said foil layer and further possesses the property of soft fold thereby failing to form a crease when subject to pressure in an amount of 2 lb/inch$^2$, selecting a sized portion of said layered sheet sufficient to cover or contain said chemical or device, orienting said plastic layer of said sheet toward said chemical or device, folding and shaping said sheet one or more times to form a protector which covers or contains said chemical or device, and subjecting said covered or contained chemical or said device to said procedure.

2. The method of claim 1 wherein prior to said selecting step, predetermined shaped and sized portions of said layered sheet are cut, stacked and packaged for use.

3. The method of claim 1 wherein said providing step further comprises applying an additional protective plastic coating to said foil layer on the side opposite the plastic layer.

4. The method of claim 1 wherein said layered sheet can be folded and unfolded along a line approximately 100 times without cracking or tearing of said foil layer.

5. The method of claim 1 further comprising the step of recycling said layered sheet for reuse by washing and drying, wherein said layered sheet does not crack or tear during said recycling step.

6. The method of claim 1 wherein said protector is selected from the group consisting of a chemical weighing dish, a chemical funnel, a chemical containment tray, a sterile pipet sheath, a chemical reaction vessel, a chemical isolation sheet, a radiochemical isolation sheet, a refoldable autoclave envelope, a septum for sample tube storage, an envelope for autoradiography, and a flexible cap for a container holding a chemical solution.

7. The method of claim 1 wherein said protector is a pipet sheath and said method further comprises removing the pipet from said sheath by sliding it along its longitudinal axis without unwrapping or tearing said sheath.

8. The method of claim 1 wherein said protector is a pipet sheath with said plastic layer of said sheet oriented toward said device, said plastic layer preventing trace-metal contamination of the pipet in said sheath during or following autoclave sterilization.

9. The method of claim 1 wherein said plastic layer provides an increased radius of curvature to folds in said layered sheet compared to a sheet of aluminum foil alone, whereby metal fatigue in said foil layer is diminished compared to such an aluminum foil alone during repeated folding.

10. The method of claim 1 wherein said providing step comprises providing a plastic layer formed from a plastic material selected from the group consisting of polyolefin and polyester.

11. The method of claim 10 wherein said plastic material is a polyolefin selected from the group consisting of polypropylene and high density polyethylene.

12. The method of claim 10 wherein said plastic material is polyethylene terephthalate.

13. The method of claim 10 wherein said plastic layer is biaxially oriented.

14. The method of claim 1 wherein said providing step comprises bonding said plastic layer to said foil layer with an agent selected from the group consisting of a bonding adhesive and an extruded laminating resin.

15. The method of claim 4 wherein said agent is polyurethane.

16. The method of claim 14 wherein said agent is high density polyethylene.

* * * * *